US005578000A

United States Patent [19]
Greff et al.

[11] Patent Number: 5,578,000
[45] Date of Patent: Nov. 26, 1996

[54] LAPAROSCOPIC SMOKE EVACUATION SYSTEM

[75] Inventors: Richard J. Greff, Yorba Linda; Bruce McLucas, Pacific Palisades, both of Calif.

[73] Assignee: Stackhouse, Inc., Riverside, Calif.

[21] Appl. No.: 376,681

[22] Filed: Jan. 23, 1995

Related U.S. Application Data

[63] Continuation of Ser. No. 6,644, Jan. 21, 1993, abandoned.

[51] Int. Cl.⁶ .................................................. H61M 31/00
[52] U.S. Cl. ............................................................ 604/22
[58] Field of Search ............................... 128/747; 606/16; 604/20, 22, 26, 35, 37, 39, 40, 42, 45, 46, 47, 264, 276, 319, 322, 405

[56] References Cited

U.S. PATENT DOCUMENTS

| | | | |
|---|---|---|---|
| 970,466 | 9/1910 | Clements et al. | 15/314 |
| 3,626,545 | 12/1971 | Sparrow | 15/314 |
| 3,810,471 | 5/1974 | Truhan | 604/45 |
| 4,562,838 | 1/1986 | Walker | 604/35 |
| 4,719,914 | 1/1988 | Johnson | 604/35 |
| 4,735,603 | 4/1988 | Goodson et al. | 128/747 |
| 4,960,419 | 10/1990 | Rosenberg | 604/22 |
| 5,047,072 | 9/1991 | Wertz et al. | 604/319 |
| 5,055,100 | 10/1991 | Olsen | 604/22 |
| 5,071,418 | 12/1991 | Rosenbaum | 604/35 |
| 5,108,389 | 4/1992 | Cosmescu | 604/35 |
| 5,160,334 | 11/1992 | Billings et al. | 604/35 |
| 5,181,916 | 1/1993 | Reynolds et al. | 606/16 |
| 5,192,267 | 3/1993 | Shapiro et al. | 604/35 |
| 5,199,944 | 4/1993 | Cosmescu | 604/26 |
| 5,226,939 | 7/1993 | Nicolas et al. | 55/309 |
| 5,234,428 | 8/1993 | Kaufman | 604/35 |
| 5,242,442 | 9/1993 | Hirschfeld | 604/35 |
| 5,264,026 | 11/1993 | Paul | 95/268 |
| 5,267,996 | 12/1993 | Fletcher | 606/16 |
| 5,269,781 | 12/1993 | Hewell, III | 604/35 |
| 5,336,169 | 8/1994 | Divillio . | |
| 5,417,655 | 5/1995 | Divillio . | |

FOREIGN PATENT DOCUMENTS 4121069  2/1992  Germany ................................ 604/35

*Primary Examiner*—Manuel Mendez
*Attorney, Agent, or Firm*—Richard L. Myers

[57] ABSTRACT

A laparoscopic smoke evacuation system for removing surgical smoke containing undesirable contaminants, including a trocar having a working channel adapted to provide access to an operative site and a stopcock communicating with the working channel. A source of vacuum is coupled through a fluid conduit to the stopcock to remove the smoke. Filtration is provided along the fluid conduit to remove the undesirable contaminants and the residual gas is exhausted to the room or the source of vacuum. A liquid collector can also be disposed along the fluid conduit together with valve means which is either mechanically or electrically operable to control application of suction to the trocar.

30 Claims, 1 Drawing Sheet

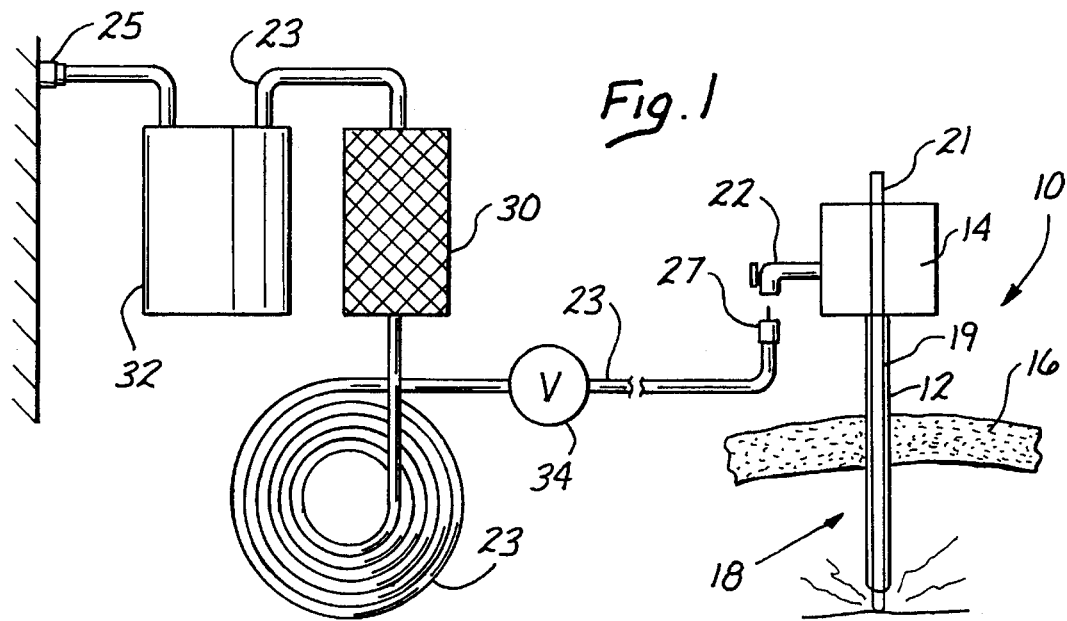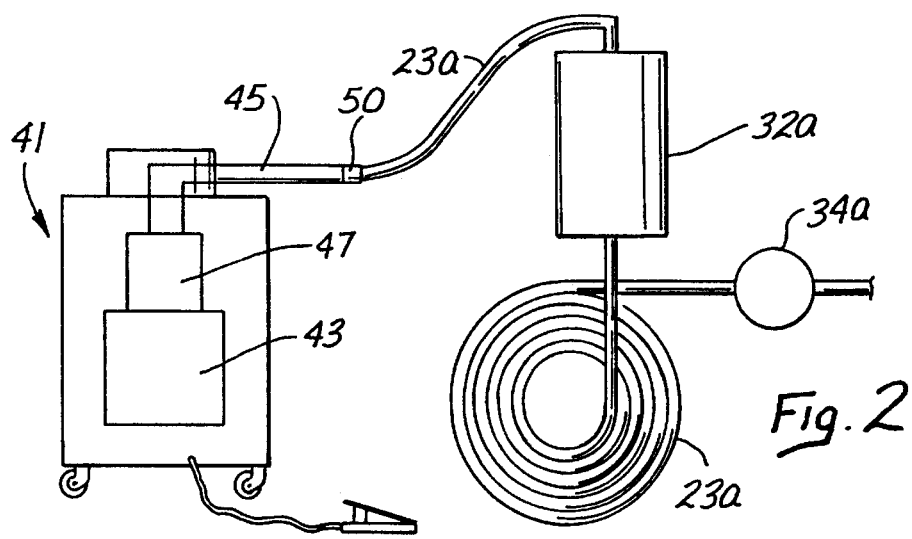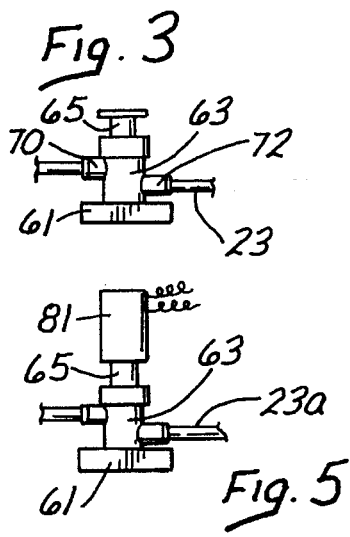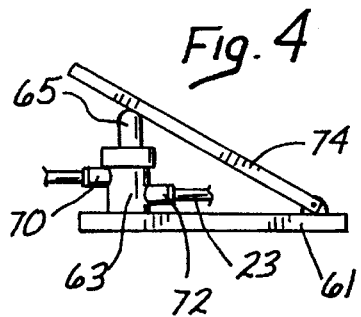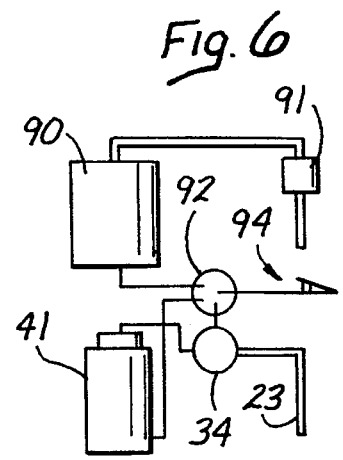

LAPAROSCOPIC SMOKE EVACUATION SYSTEM

This application is a continuation of application Ser. No. 08/006,644, filed Jan. 21, 1993 now abandoned.

BACKGROUND OF THE INVENTION

1. Field of the Invention

This invention relates generally to methods and apparatus for evacuating surgical smoke from an operative site, and more specifically to such apparatus and methods which are adapted for laparoscopic surgery.

2. Discussion of the Prior Art

Laparoscopic surgery has become increasingly popular as a less invasive technique for performing abdominal surgery. Trocars are commonly used to puncture the lapra or abdomen and establish a working channel into the abdominal cavity. A particular operation may require several trocars, each providing access for one or more instruments involved in the surgery. For example, an endoscope may be inserted in one trocar while retractors, scalpels, staplers, and other surgical devices are individually inserted through other trocars.

As part of the surgical process, the abdomen is typically inflated with an insufflation gas which tends to separate the interior organs and also to provide a generally enlarged cavity within which to perform the surgery. Laparoscopes which are commonly used in this type of surgery are configured to permit introduction of the insufflation gas directly into the abdominal cavity. The trocars are constructed with seals which prevent the escape of the insufflation gasses both in the presence and absence of an instrument.

When a particular surgery requires that tissue be cut, lasers and electrocautery devices are often preferred as they are easily manipulated and produce relatively clean cuts. They also have a cauterizing effect and therefore limit bleeding. However, cutting with lasers and electrocautery devices often produces smoke and, if the cut tissue is diseased, the smoke may contain toxic, odiferous, and otherwise undesirable contaminants.

The removal and filtration of this smoke is important, since this smoke tends to cloud the surgeon's view of the operative site. In spite of these significant needs to remove the smoke, this is not accomplished without considerable complication. Due to the confines of the abdomen, there is very little access to the surgical site, and the trocars are jealously reserved for instruments more directly associated with the surgery.

In the past, the contaminated surgical smoke has been evacuated by opening the stopcock on one of the trocars and letting the insufflation gas carry the smoke into the operating room. This not only slows the surgery requiring that the abdominal cavity be again insufflated, but it also subjects the surgeon and his staff to the smoke contaminants. Recirculating systems have been used which incorporate two trocars in a closed system. The smoke is withdrawn through one trocar, typically using a probe, and then filtered and reintroduced through the other trocar. Although the smoke in this recirculation system is filtered, the toxic gasses that result from both laser and electrocautery surgery are not filtered and consequently are recirculated back to the patient.

A smoke evacuation kit of the past has also been provided for use with an elongate probe. This probe has been adapted for insertion through the seals of the trocar and into the working channel in order to reach the operative site. This type of smoke evacuation probe is particularly undesirable, since it occupies the working channel rendering the trocar useless for other surgical devices.

SUMMARY OF THE INVENTION

These deficiencies of the prior art are avoided in the present invention by a system which includes a flexible conduit adapted to be connected between the operative site and a source of vacuum. The conduit is connected to the stopcock on a trocar and gains access to the operative site in the space between the working channel and any instrument which may be inserted in the trocar to perform a surgical function. The other end of the conduit is attached to a source of vacuum such as wall vacuum or an independent, standalone smoke evacuator. Along the conduit a filter can be provided to remove the undesirable contaminants from the smoke with the remainder of the harmless gasses evacuated to the wall vacuum or released to the operating room. A fluid canister can also be provided along the fluid conduit to remove any liquids which may be present in the conduit.

In a preferred embodiment, a valve is disposed along the fluid conduit to provide mechanical or electrical means for controlling application of the vacuum to the trocar. Various devices are disclosed for simultaneously activating one or more of the cutting devices (such as a laser), the valve, and the smoke evacuator.

These and other features and advantages of the invention will become more apparent with a description of preferred embodiments and reference to the associated drawings.

DESCRIPTION OF THE DRAWINGS

FIG. 1 is a schematic view of one embodiment of the present invention including a fluid conduit connected between the stopcock of the trocar and a source of wall vacuum;

FIG. 2 is a schematic view of a further embodiment of the invention wherein the fluid conduit is connected to a stand-alone smoke evacuator;

FIG. 3 is a side elevation view of a mechanical hand valve adapted for controlling flow of a fluid through the conduit;

FIG. 4 is a side elevation view of a mechanical foot valve adapted to be used with the present invention;

FIG. 5 is a side elevation view of a electrical valve adapted for use with the present invention; and FIG. 6 is a schematic view of a further embodiment where one or more of a cutter, smoke evacuator, and valve can be simultaneously activated.

DESCRIPTION OF THE PREFERRED EMBODIMENTS

A trocar is illustrated in FIG. 1 and designated by the reference numeral 10. The trocar includes an elongate cannula 12 and a seal housing 14. The cannula 12, which may have an inside diameter typically between 5 mm and 10 mm, is adapted to be disposed across a body wall, such as the abdominal wall 16 to provide access to an interior cavity, such as the abdominal cavity 18. In providing this access, a working channel 19 extending through the seal housing 14 and cannula 12 provides access for various surgical instruments, from outside the abdominal wall 16 into the abdominal cavity 18. These surgical instruments, which may include a laser probe for example, are collectively represented by the instrument 21 in FIG. 1.

The trocar 10 also includes a valve or stopcock 22 which is typically attached to the seal housing 14 and provides access to the working channel 19. In the past, a laparoscope (not shown) has been used to inflate the abdominal cavity 18 with an insufflation gas, such as carbon dioxide, to enlarge the cavity and also provide for the separation of interior organs. This insufflation typically occurs at a flow rate of six to fifteen liters per minute.

Seals (not shown) are typically disposed within the seal housing 14 and prevent the escape of the insufflation gasses through the trocar 10. Two seals are normally provided, one which functions in the absence of the instrument 21, and the other which functions in the presence of the instrument 21. As many as three or four trocars may be used in a single operation each providing access to the abdominal cavity 18 and each forming a working channel which is shared by multiple surgical instruments.

When it is desirable to cut tissue within the abdominal cavity 18, various instruments such as lasers and electrocautery devices can be inserted through the trocar 10. While these devices are highly advantageous, they tend to produce a surgical smoke which may contain undesirable contaminants such as toxic and odiferous gasses. It is one of the purposes of the present invention to withdraw the surgical smoke from the operative site, to filter the smoke and thereby remove the undesirable contaminants, and to exhaust the filtered gasses.

In order to accomplish this purpose, the present invention provides suction at the stopcock 22 of the trocar 10 of a magnitude sufficient to produce a flow rate of three to thirty liters per minute. This is accomplished by providing a fluid conduit 23 between the trocar 10 and a source of vacuum. In the FIG. 1 embodiment, this vacuum source includes wall vacuum which is piped to the operating room and provides suction typically in the range of one hundred to four hundred inches of water. This wall vacuum is structurally available at the wall of the operating room through a connector 25.

The fluid conduit 23 in a preferred embodiment includes multiple lengths of plastic tubing typically formed from a polyvinylchloride and having an inside diameter such as 3/16 inch. A male Luer lock 27 is provided at the distal end of the conduit 23 and facilitates direct attachment to the stopcock 22 of the trocar 10.

In an appropriate location along the conduit 23, a filter 30 can be provided. The contents of this filter 30 should be appropriate for removing the undesirable contaminants, but the filter should also be chosen to provide an appropriate pressure drop along the conduit 23. This pressure drop across the filter 30 is preferably in a range between eighteen and forty inches of water at a flow rate of two cubic feet per minute. In a preferred embodiment, the filter 30 is manufactured by Stackhouse, Inc. and sold under the model number ILF-100. This particular filter 30 provides a pressure drop of approximately twenty-five inches of water at two cubic feet per minute. This provides an adequate flow through the filter 30 as vacuum is applied to the trocar 10. A fluid canister 32 can also be provided along the conduit 23 to remove any fluids which may have become trapped in the conduit. These fluids may be drawn from the operative site or may have resulted from condensation within the conduit 23. The fluid canister 32 may be placed ahead or after the filter 30 in the conduit.

It is generally undesirable for vacuum to be applied continuously to the surgical site. Continuous vacuum not only requires a large volume of insufflation gas but also has a tendency to dry and cool the tissue. As a consequence continuous vacuum adversely affects the pneumoperitoneum or insufflation of the abdominal cavity 18. For these reasons a preferred embodiment of the invention includes a valve 34 disposed along the conduit 23. This valve 34 can take various forms, as described in greater detail below, but will function to control the application of vacuum to the trocar 10. This control in different embodiments may be digital (on or off), or variable within a preferred range of suction. In a preferred embodiment, the valve 34 is disposed along the conduit approximately six feet from the Luer fitting 27 and approximately sixteen feet from the filter 30.

A further embodiment of the invention is illustrated in FIG. 2 wherein elements having similar characteristics are designated by the same reference numeral followed by the lower case letter "a". For example, this embodiment includes a valve 34a, fluid canister 32a both of which are disposed along a conduit 23a. As in the previous embodiment, the proximal end of the conduit 23a is adapted for attachment to the stopcock 22 of the trocar 10.

At the opposite end, the conduit 23a is coupled to a source of vacuum in the form of a smoke evacuator 41. This evacuator 41 is a stand-alone apparatus such as that disclosed in applicant's copending application Ser. No. 780,768 filed on Oct. 22, 1991 and entitled Surgical Smoke Evacuator. The evacuator 41 includes a motor and impeller combination 43 which produces a vacuum and draws air through an input hose and a filter 47. After filtering, this air is exhausted to the room, such as the operating room, where the surgery is being conducted. The input hose 45 typically has an inside diameter of 7/8 inch so that an adapter 50 may be required to align the hose 45 with the conduit 23a.

A filter, such as that designated by the reference numeral 30 in FIG. 1, may also be provided in this embodiment although the filter 47 within the evacuator 41 may be sufficient. A fluid canister 32a could also be advantageously included in this combination.

In a preferred embodiment illustrated in FIG. 3, the valve 34 is adapted to mechanically control the application of vacuum to the trocar 10. In its simplest form, the valve 34 might function as a hand valve with a base 61, an upstanding housing 63, and a plunger 65. The housing 63 is hollow and communicates through external ports 70 and 72 with the conduit 23. The plunger 65 is suitably channeled to block fluid flow between the ports 70 and 72 in an extended position and facilitate communication between the ports 70 and 72 in a compressed position. A compression spring can be provided to bias the plunger 65 to the extended position. Operation of this valve 34 would be accomplished by moving the plunger 65 to the compressed position, for example by squeezing the valve between the fingers and palm of the user's hand.

In another embodiment illustrated in FIG. 4, the mechanical valve 34 is operable by a user's foot. This embodiment could include a structure similar to that illustrated in FIG. 3 but with a foot plate 74 pivotal on the base 61 to move the plunger 65 to the compressed position.

In still a further embodiment illustrated in FIG. 5 the valve 34 is electrically actuated, for example, by providing a solenoid 81 operatively disposed relative to the plunger 65. By electrically actuating the solenoid 81, the plunger 65 could be moved to its compressed state thereby facilitating fluid communication between the source of vacuum, such as the evacuator 41, and the trocar 10.

In a system such as that illustrated in FIG. 6, which includes a laser 90 and laser probe 91, a common switch 92 can be provided to simultaneously actuate two or more of the elements associated with the present invention. For example, a mechanical or electrical switch 92 could be operated by a foot pedal 94 to simultaneously actuate two or more of the laser 90, the evacuator 41, and the valve 34. A system coupling all three elements is particularly advantageous since it simultaneously activates the laser 90 which produces the smoke, activates the evacuator 41 to provide the source of vacuum, and opens the conduit 23 to enable that vacuum to remove the smoke through the trocar 10.

The method of the present invention is of particular interest, since as it takes advantage of readily available wall vacuum and applies it to structure, namely the stopcock 22, which is already present and in place in a normal laparoscopic surgery. Since the abdominal cavity 18 of a patient is only about two liters in volume, a relatively low flow rate is required in order to remove smoke from the cavity. This smoke removal, which is intended to facilitate visualization of the operative site, generally requires that a full gas exchange be undertaken within the abdominal cavity. In other words, approximately two liters of gas must be removed from the abdominal cavity. It is desirable that this removal be accomplished in a time interval which is slow enough to permit reinsufflation of the abdominal cavity but fast enough to permit a rapid gas exchange. It would typically be advisable to perform this gas exchange in four to sixteen seconds. This time period equates to a flow rate between 7.5 liters per minute and 30 liters per minute. In a preferred method, the gas exchange is completed within four to eight seconds and with flow rates between fifteen and thirty liters per minute.

One might normally think that the comparatively high flow rates of fifty to eighty liters per minute provided by wall vacuum would be totally inapplicable for this smoke evacuation. However, this is not necessarily the case. By connecting the wall vacuum to the stopcock 22 and providing sufficient flow restriction along the path of the conduit 23, an appropriate flow rate can be achieved.

Connection of the conduit 23 to the stopcock 22 not only takes advantage of the existing structure of the trocar 10, but also takes advantage of a relatively small orifice which exists in the typical stopcock. This orifice may have a diameter of about 0.075 inches so that it provides a significant flow restriction to any fluid passing through the stopcock 22. Of course each of the elements along the conduit 23 also contribute to flow restriction, but this orifice in the stopcock 22 will typically account for more than half of the drop in the flow rate.

A stand-alone source of vacuum, such as the smoke evacuator 41 can also be employed to achieve these flow rates. For example, the smoke evacuator 41 can be provided in the form of applicant's Smoke Evacuator Model ST-2500. Using this source of vacuum, flow rates between 9 and 16 liters per minute have been achieved.

In a preferred method, the trocar 10 is inserted through the abdominal wall 16 into the abdominal cavity 18. The conduit 23 is attached at one end to a source of vacuum, such as the wall vacuum at the connector 25 or the surgical smoke evacuator 41. The proximal end of the conduit 23 is connected to the stopcock 22 of the trocar 10. The filter 30 and canister can be provided along the conduit 23 along with the valve 34.

As the laparoscopic surgery progresses, the surgeon's view of the abdominal cavity typically through a laparoscope will indicate that the smoke needs to be evacuated. At this point, the valve 34 can be selectively activated to facilitate fluid flow from the operative site. When sufficient smoke has been evacuated, the valve 34 can be selectively deactivated to block fluid flow from the operative site. In the preferred method, this operation of the valve 34 requires that the valve be activated for a duration of about four to eight seconds.

Although the invention has been disclosed with reference to preferred embodiments of the concept, it will be apparent that the concept can be embodied in other elements and combinations of elements all within the scope of the concept. For example, the valve 34 can be provided in many different forms, either mechanical or electrical to control the application of vacuum to the trocar 10. Elements other than the filter 30 and the canister 32 can also be added in the fluid path of the fluid conduit 23 to otherwise process the smoke being removed from the operative site. Other sources of vacuum can also be provided, although the wall vacuum and evacuator 41 are commonly available in an operating room.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A laparoscopic smoke evacuation system for removing from an operative site, smoke containing undesirable contaminants, the evacuator comprising:

a trocar having a working channel and being adapted for operative disposition across a body wall with the working channel of the trocar providing access to the operative site;

a valve coupled to the trocar and communicating with the working channel;

a source of wall vacuum disposed in a wall of an operating room proving a high suction at a flow rate of about forty to about eighty liters per minute, a fluid conduit connected between the valve of the trocar and the source of the wall vacuum;

a filter disposed along the fluid conduit for applying a first predetermined reduction in suction, and for separating the smoke into the undesirable components and a residual gas, the conduit, the filter, and the working channel forming a passage for conducting the smoke from the operative site to the source of wall vacuum;

means defining a flow restriction along the passage to thereby generate a second predetermined reduction in suction, the restriction being of a size sufficiently small to produce a reduction in the flow rate to a range between about ten and about fifty-five liters per minute; and means included in the fluid conduit for exhausting the residual gas into the source of wall vacuum.

2. The laparoscopic smoke evacuator system recited in claim 1 wherein the valve is a first valve and the system further comprises a second valve disposed along the passage for controlling the application of the wall vacuum to the first valve.

3. The laparoscopic smoke evacuation system recited in claim 1 further comprising liquid collection means disposed along the passage for collecting liquid flowing along the conduit from the trocar to the source of wall vacuum.

4. A laparoscopic smoke evacuation system recited in claim 2 wherein the second valve has properties for being manually actuated.

5. A laparoscopic smoke evacuation system recited in claim 4 wherein the second valve includes a foot pedal having properties for being depressed by the foot of the user to manually actuate the second valve.

6. A laparoscopic smoke evacuation system recited in claim 2 wherein the second valve has properties for being electrically actuated.

7. A laparoscopic smoke evacuation system recited in claim 6 further comprising:
   a laser providing a source of laser energy;
   probe means coupled to the laser for delivering the laser energy to the operative site; and
   switch means for simultaneously activating the laser and the second valve.

8. The laparoscopic smoke evacuation system recited in claim 1 wherein the means defining the flow restriction comprises portions of the first valve which defines an orifice along the passage.

9. The laparoscopic smoke evacuation system recited in claim 1 further comprising electrocautery apparatus operable at the operative site to produce the smoke.

10. A laparoscopic smoke evacuator system for removing from an operative site, smoke containing undesirable contaminants, the system comprising:
    a trocar having a working channel and being adapted for operative disposition across a body wall with the working channel of the trocar providing access to the operative site;
    a first valve disposed on the trocar and communicating with the working channel;
    a source of wall vacuum disposed in a wall of an operating room proving a high suction at a flow rate of about forty to about eighty liters per minute,
    means for conducting the smoke along a fluid path extending between the first valve of the trocar and the surgical smoke evacuator;
    a filter disposed along the fluid path for applying a first predetermined reduction in suction, and for separating the smoke into the undesirable components and a residual gas, the fluid path, the filter, and the working channel forming a passage for conducting the smoke from the operative site to the source of wall vacuum; and
    a second valve disposed along the fluid path for controlling application of the vacuum from the smoke evacuator, through the first valve and to the operative site.

11. The laparoscopic smoke evacuation system recited in claim 8 wherein the second valve has properties for being electrically actuated.

12. The laparoscopic smoke evacuator system recited in claim 11 wherein the second valve includes switch means for electrically actuating the smoke evacuator in order simultaneously to produce a vacuum at the smoke evacuator and to control application of the vacuum from the smoke evacuator through the first valve to the operative site.

13. A laparoscopic smoke evacuation system recited in claim 10 wherein the second valve has properties for being manually actuated.

14. The laparoscopic smoke evacuation system recited in claim 10 further comprising:
    a laser providing a source of laser energy;
    probe means connected to the laser for delivering the laser energy to the operative site; and
    switch means for simultaneously activating the laser and actuating the second valve.

15. The laparoscopic smoke evacuation system recited in claim 10 wherein smoke is produced at the operative site by operation of an electrocautery apparatus.

16. The laparoscopic smoke evacuation system recited in claim 10 wherein the filter is disposed in the surgical smoke evacuator.

17. The laparoscopic smoke evacuation system recited in claim 10 further comprising liquid collection means disposed along the fluid path for collecting liquid flowing along the path from the trocar to the smoke evacuator.

18. A method for evacuating smoke from a surgical site in the abdominal cavity during laparoscopic surgery, the smoke containing undesirable contaminants, the method comprising the steps of:
    inserting a trocar into the surgical site, the trocar having a working channel providing access to the surgical site and a stopcock extending into the channel, the stopcock outputting a low-suction vacuum to the working channel;
    manipulating an instrument through the working channel of the trocar to the operative site;
    coupling a flexible conduit between a high-suction source of wall vacuum disposed in a wall of an operating room and the valve of the trocar to draw the smoke from the operative site, through the working channel having low-suction vacuum, exteriorly of the instrument and to the high-suction source of wall vacuum; and
    filtering the undesirable contaminants from the smoke by providing a filter along the flexible conduit between the stopcock outputting the low-suction vacuum and the high-suction source of wall vacuum, the filter applying a predetermined reduction in the high-suction vacuum to thereby output a relatively low-suction vacuum.

19. The method recited in claim 18 wherein the coupling step includes a step of providing a source of wall vacuum and coupling the flexible conduit to the source of wall vacuum.

20. The method recited in claim 18 further comprising the step of controlling the flow of fluid between the stopcock and the source of vacuum.

21. The method recited in claim 18 wherein the coupling step includes the step of providing a portable surgical smoke evacuator and coupling the flexible conduit to the smoke evacuator.

22. The method recited in claim 18 further comprising the step of:
    restricting fluid flow between the source of vacuum and the trocar so that the rate of fluid flow in the working channel is in a range between fifteen and thirty liters per minute.

23. The method recited in claim 20 wherein the valve is a first valve and the controlling step includes the steps of:
    providing a second valve along the flexible conduit to selectively facilitate and block the flow of fluid from the surgical site;
    selectively actuating the second valve to evaluate the smoke from the abdominal cavity; and
    selectively deactivating the second valve when the abdominal cavity is fully evacuated.

24. The method recited in claim 23 wherein the step of selectively activating the second valve has a duration of about four to eight seconds.

25. The method recited in claim 18 wherein the coupling step includes the step of drawing the smoke from the operative site at a flow rate having a range between about 7.5 liters per minute and about 30 liters per minute.

26. The method recited in claim 25 wherein the flow rate has a range between about 15 liters per minute and about 30 liters per minute.

27. The laparoscopic smoke evacuator system recited in claim 8 wherein the diameter of the orifice is about 0.075 inches.

28. A combination for removing surgical smoke from a surgical operating room, comprising;

a plurality of walls defining the surgical operating room and including a sidewall;

a high-suction source of wall vacuum disposed outside the room exteriorly of the sidewall;

means for coupling the high-suction source of wall vacuum through the side wall to provide high-suction wall vacuum interiorly of the room, the high-suction wall vacuum having a flow rate of about 40–80 liters per minute;

a trocar for receiving a low-suction flow rate of about 10–55 liters per minute, the trocar having a working channel and being disposed at an operative site within the surgical operating room;

a valve coupled to the trocar and communicating with the working channel;

a fluid conduit extending between the valve of the trocar and the coupling means associated with the high-suction source of wall vacuum, the working channel of the trocar, the conduit, and the coupling means defining an exhaust passage extending through the sidewall of the surgical operating room;

means defining a predetermined flow restriction along the exhaust passage, the predetermined flow restriction being of a size sufficiently small to produce the reduction in the suction flow rate to the range between about 10 and about 55 liters per minute; whereby the exhaust passage conducts the surgical smoke from the operative site interiorly of the operating room and through the sidewall to regions exterior of the room.

29. A method for evacuating smoke from a surgical site, the method comprising the steps of:

providing an operating room defined by at least one sidewall and having a coupling extending through the one sidewall to present high-suction wall vacuum interiorly of the operating room;

providing a trocar at the surgical site within the operating room, the trocar receiving a low-suction flow rate of about 10–55 liters per minute, and having a working channel and a valve extending into the working channel;

providing a conduit having a proximal end and a distal end, and a length sufficient to extend from the high-suction wall vacuum coupling to the trocar at the surgical site;

attaching the proximal end of the conduit to the wall vacuum coupling, the conduit having a length sufficient to extend from the high-suction wall vacuum coupling to the trocar at the surgical site;

attaching the distal end of the conduit to the valve of the trocar; and evacuating the smoke from the surgical site through the working channel and the valve of the trocar at the low-suction flow rate and through the conduit and the coupling of the high-suction wall vacuum to regions exterior of the operating room.

30. A portable, lightweight, and inexpensive laparoscopic smoke evacuation system for converting conventional liquid-evacuating forces, characterized by high-suction and low-volume, to smoke-removing forces, characterized by low-suction and high-volume, the apparatus comprising:

a connector for connecting to a source of wall vacuum, the source of wall vacuum providing the conventional high-suction, low-volume liquid-evacuating forces at a suction of between 100 and 400 inches of water, the source of wall vacuum being designed for evacuating liquids such as blood from an operating room at both a low volume and a high suction, the liquid-removing suction of between 100 and 400 inches of water being entirely too great to be applied to a conventional laparoscopic smoke evacuation system;

a fluid conduit operatively connected to the connector;

a filter disposed along the fluid conduit, the filter being specifically engineered for significantly reducing the suction from the wall vacuum by approximately 25 inches of water, the filter further being engineered for separating smoke into undesirable components and a residual gas;

a stopcock disposed along the fluid conduit, the stopcock having a relatively small orifice, which is utilized to further significantly reduce the suction from the wall vacuum, the small opening of the stopcock reducing a flow rate of the stopcock by at least 50 percent to thereby generate and output the low-suction, high-volume, smoke-evacuating forces; and a trocar operatively connected to the stopcock, the trocar receiving the low-suction, high-volume, smoke-evacuating forces from the stopcock, the trocar having a working channel and being adapted for operative disposition across a body wall with the working channel of the trocar providing access to an operating site.

* * * * *